US009629707B2

(12) United States Patent
Ferragamo et al.

(10) Patent No.: US 9,629,707 B2
(45) Date of Patent: *Apr. 25, 2017

(54) ATTACHMENT DEVICE TO ATTACH TISSUE GRAFT

(71) Applicant: Smith & Nephew, Inc., Memphis, TN (US)

(72) Inventors: Michael Charles Ferragamo, Foster, RI (US); Jeffrey Wyman, Naples, FL (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/457,455

(22) Filed: Aug. 12, 2014

(65) Prior Publication Data
US 2015/0094763 A1 Apr. 2, 2015

Related U.S. Application Data

(63) Continuation of application No. 13/248,635, filed on Sep. 29, 2011, now Pat. No. 8,834,523.

(51) Int. Cl.
A61B 17/04 (2006.01)
A61F 2/08 (2006.01)

(52) U.S. Cl.
CPC ........ A61F 2/0811 (2013.01); A61B 17/0401 (2013.01); A61B 2017/0403 (2013.01);
(Continued)

(58) Field of Classification Search
CPC ........ A61B 17/0401; A61B 2017/0409; A61B 2017/0414; A61B 2017/0458;
(Continued)

(56) References Cited

U.S. PATENT DOCUMENTS 5,306,301 A * 4/1994 Graf et al. ..................... 606/232
5,356,413 A * 10/1994 Martins et al. ................. 606/75
(Continued)

OTHER PUBLICATIONS

First Office Action for related Chinese Application No. 201280047736.3, issued on May 26, 2015.
(Continued)

Primary Examiner — Amy R Weisberg
(74) Attorney, Agent, or Firm — Burns & Levinson LLP; Joseph M. Maraia

(57) ABSTRACT

A tissue graft attachment device includes a platform member including a leading edge and a trailing edge connected to the leading edge by a pair of sides. The platform member defines a pair of slots extending along a longitudinal axis passing between the leading edge and the trailing edge, and an opening between the pair of slots and the leading edge. The device includes a first suture passing through the opening, a second suture passing through one of the slots, and an attachment member passing through the pair of slots to form a loop. A method for attaching a tissue graft includes providing the tissue graft attachment device, forming a bone tunnel, pulling on the first suture to pull the platform member through the bone tunnel, and pulling on the second suture to position the platform member on the bone tunnel.

20 Claims, 4 Drawing Sheets

(52) U.S. Cl.
CPC . *A61B 2017/044* (2013.01); *A61B 2017/0404* (2013.01); *A61B 2017/0406* (2013.01); *A61B 2017/0408* (2013.01); *A61F 2002/0852* (2013.01); *A61F 2002/0882* (2013.01)

(58) Field of Classification Search
CPC ........ A61B 17/0466; A61B 2017/0496; A61B 17/06166; A61B 2017/0404; A61B 2017/0403; A61B 2017/0408; A61F 2/0811; A61F 2002/0882; A61F 2002/0852
USPC ...... 606/232, 74, 103; 24/115 R, 128, 129 R
See application file for complete search history.

(56) References Cited

U.S. PATENT DOCUMENTS

| | | | | |
|---|---|---|---|---|
| 5,372,599 | A * | 12/1994 | Martins | 606/75 |
| 5,505,735 | A * | 4/1996 | Li | 623/13.14 |
| 5,645,588 | A * | 7/1997 | Graf et al. | 606/151 |
| 5,769,894 | A * | 6/1998 | Ferragamo | 606/148 |
| 5,950,284 | A * | 9/1999 | Persson | 24/129 R |
| 5,964,764 | A * | 10/1999 | West et al. | 606/232 |
| 6,017,346 | A * | 1/2000 | Grotz | 606/232 |
| 6,086,591 | A * | 7/2000 | Bojarski | 606/64 |
| 6,093,201 | A * | 7/2000 | Cooper et al. | 606/232 |
| 6,117,139 | A * | 9/2000 | Shino | 606/86 R |
| 6,117,161 | A * | 9/2000 | Li et al. | 606/232 |
| 6,193,754 | B1 * | 2/2001 | Seedhom | 623/13.11 |
| 6,514,274 | B1 * | 2/2003 | Boucher et al. | 606/232 |
| 6,517,578 | B2 * | 2/2003 | Hein | 623/13.13 |
| 6,533,802 | B2 * | 3/2003 | Bojarski et al. | 606/232 |
| 7,097,654 | B1 * | 8/2006 | Freedland | 606/232 |
| 7,144,415 | B2 * | 12/2006 | Del Rio et al. | 606/232 |
| 7,500,983 | B1 * | 3/2009 | Kaiser et al. | 606/232 |
| 7,530,990 | B2 * | 5/2009 | Perriello et al. | 606/232 |
| 7,594,923 | B2 * | 9/2009 | Fallin et al. | 606/232 |
| 7,819,898 | B2 * | 10/2010 | Stone et al. | 606/232 |
| 7,967,843 | B2 * | 6/2011 | Kaiser et al. | 606/232 |
| 8,109,965 | B2 * | 2/2012 | Stone et al. | 606/232 |
| 8,162,997 | B2 * | 4/2012 | Struhl | 606/300 |
| 8,231,674 | B2 * | 7/2012 | Albertorio et al. | 623/13.14 |
| 8,323,338 | B2 * | 12/2012 | LeBeau et al. | 623/13.14 |
| 8,398,678 | B2 * | 3/2013 | Baker et al. | 606/213 |
| 8,591,578 | B2 * | 11/2013 | Albertorio et al. | 623/13.13 |
| 2001/0041938 | A1 * | 11/2001 | Hein | 623/13.13 |
| 2002/0173788 | A1 * | 11/2002 | Bojarski et al. | 606/60 |
| 2003/0216780 | A1 * | 11/2003 | Fitts et al. | 606/232 |
| 2004/0015171 | A1 * | 1/2004 | Bojarski et al. | 606/72 |
| 2004/0098053 | A1 * | 5/2004 | Tran | 606/232 |
| 2007/0049944 | A1 * | 3/2007 | Stone et al. | 606/72 |
| 2007/0233241 | A1 * | 10/2007 | Graf et al. | 623/13.14 |
| 2007/0270857 | A1 * | 11/2007 | Lombardo et al. | 606/72 |
| 2008/0046009 | A1 * | 2/2008 | Albertorio et al. | 606/232 |
| 2008/0125779 | A1 * | 5/2008 | Ferree | 606/61 |
| 2008/0154314 | A1 * | 6/2008 | McDevitt | 606/304 |
| 2008/0275554 | A1 * | 11/2008 | Iannarone et al. | 623/13.14 |
| 2008/0287991 | A1 * | 11/2008 | Fromm | 606/232 |
| 2009/0248028 | A1 * | 10/2009 | Alexander | 606/103 |
| 2010/0063541 | A1 * | 3/2010 | Brunelle et al. | 606/232 |
| 2010/0125297 | A1 * | 5/2010 | Guederian et al. | 606/232 |
| 2010/0256677 | A1 * | 10/2010 | Albertorio et al. | 606/232 |
| 2010/0268273 | A1 * | 10/2010 | Albertorio et al. | 606/232 |
| 2010/0324676 | A1 * | 12/2010 | Albertorio et al. | 623/13.14 |
| 2010/0331612 | A1 * | 12/2010 | Lashinski et al. | 600/37 |
| 2011/0077667 | A1 * | 3/2011 | Singhatat et al. | 606/139 |
| 2011/0125189 | A1 * | 5/2011 | Stoll et al. | 606/232 |
| 2011/0137342 | A1 * | 6/2011 | Henderson et al. | 606/232 |
| 2011/0184227 | A1 * | 7/2011 | Altman et al. | 600/37 |
| 2011/0301708 | A1 * | 12/2011 | Stone et al. | 623/13.14 |
| 2012/0046747 | A1 * | 2/2012 | Justin et al. | 623/13.14 |
| 2012/0059416 | A1 * | 3/2012 | Justin et al. | 606/232 |
| 2012/0116452 | A1 * | 5/2012 | Stone et al. | 606/232 |
| 2012/0123541 | A1 * | 5/2012 | Albertorio et al. | 623/13.14 |
| 2012/0130373 | A1 * | 5/2012 | Larroque-Lahitette | 606/74 |
| 2012/0245630 | A1 * | 9/2012 | Napolitano et al. | 606/232 |
| 2012/0290002 | A1 * | 11/2012 | Astorino | 606/232 |
| 2013/0035720 | A1 * | 2/2013 | Perriello et al. | 606/232 |
| 2013/0096612 | A1 * | 4/2013 | Zajac et al. | 606/232 |
| 2013/0204299 | A1 * | 8/2013 | Mantovani et al. | 606/232 |
| 2013/0204366 | A1 * | 8/2013 | Spenciner et al. | 623/13.14 |
| 2013/0245700 | A1 * | 9/2013 | Choinski | 606/300 |
| 2013/0261677 | A1 * | 10/2013 | Bouduban et al. | 606/323 |
| 2013/0268073 | A1 * | 10/2013 | Albertorio et al. | 623/13.12 |
| 2013/0289574 | A1 * | 10/2013 | Shinde | 606/96 |
| 2015/0094742 | A1 * | 4/2015 | Spenciner | 606/151 |

OTHER PUBLICATIONS

Examination Report from related Australian Application No. 2012315905 issued May 10, 2016.

* cited by examiner

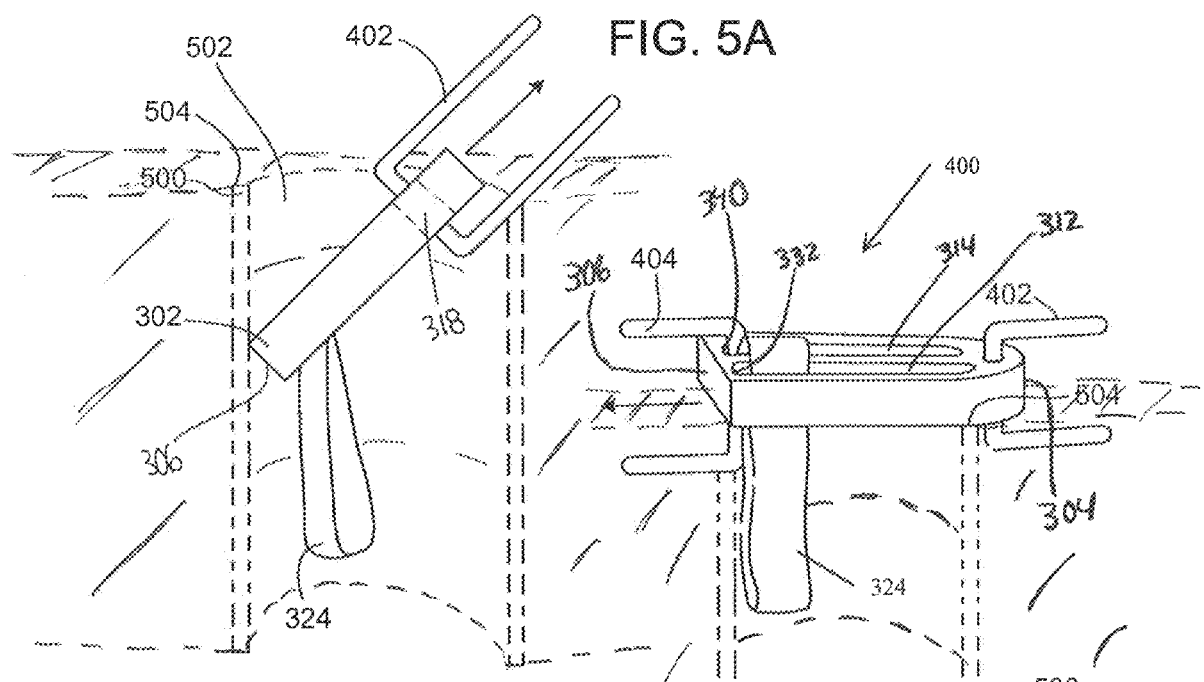
FIG. 5A
FIG. 5B
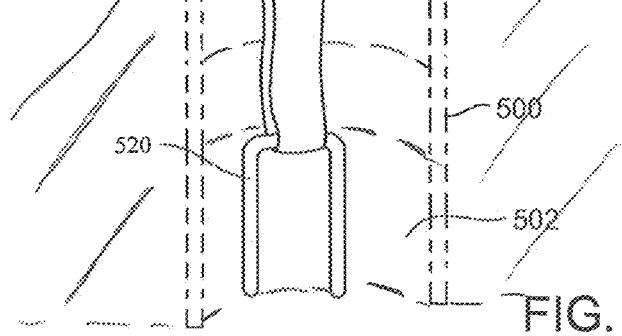
FIG. 5C

ATTACHMENT DEVICE TO ATTACH TISSUE GRAFT

CROSS-REFERENCE TO RELATED APPLICATIONS

This application is a continuation of, and claims priority from, U.S. application Ser. No. 13/248,635, filed Sep. 29, 2011. The contents of the prior application is incorporated herein by reference in their entirety.

TECHNICAL FIELD

This document relates to tissue graft attachment.

BACKGROUND

An anterior cruciate ligament (ACL) that has ruptured and is non-repairable is generally replaced arthroscopically by a tissue graft. The tissue graft can be harvested from a portion of a patellar tendon having so called "bone blocks" at each end, and from the semitendonosis and gracilis. Alternatively, the tissue graft can be formed from synthetic materials or from a combination of synthetic and natural materials.

The replacement tissue graft is implanted by securing one end of the tissue graft in a socket formed in a passage within the femur, and passing the other end of the graft through a passage formed in the tibia. Generally, sutures are used to affix each end of the tissue graft to a fastener (e.g., an interference screw or a post), which is then secured to the bone.

A graft fixation member, e.g., a fixation button, can be used to secure the tissue graft at the femoral cortex, as described in U.S. Pat. No. 5,306,301 ("the '301 patent") hereby incorporated by reference in its entirety. When using a fixation button, the femoral passage generally includes a relatively larger diameter portion for receiving the graft, and a smaller diameter, passing channel near the femoral cortex for receiving a length of suture that runs from the tissue graft to the fixation button. By measuring the total length of the femoral passage and the length of the larger diameter portion of the femoral passage, the surgeon determines the appropriate length of suture material for attaching the fixation button to the tissue graft.

SUMMARY

According to one aspect, a tissue graft attachment device includes a platform member including a leading edge and a trailing edge connected to the leading edge by a pair of sides. The platform member defines a pair of slots extending along a longitudinal axis passing between the leading edge and the trailing edge, and an opening between the pair of slots and the leading edge. The tissue graft attachment device includes a first suture passing through the opening, a second suture passing through one of the slots, and an attachment member passing through the pair of slots to form a loop.

Implementations of this aspect may include one or more of the following features.

The pair of sides taper from the trailing edge toward the leading edge. The pair of slots taper from the trailing edge toward the leading edge. The pair of slots are formed on opposite sides of a central axis that passes between the leading edge and the trailing edge. The opening is formed on the central axis. The leading edge is substantially curved, for example, substantially semi-circular. The trailing edge is substantially straight relative to the leading edge. The opening has a substantially circular cross-section. The attachment member is a third suture or an elastic band.

According to another aspect, a method for attaching a tissue graft includes providing the tissue graft attachment device, forming a bone tunnel, pulling on the first suture to pull the platform member through the bone tunnel, and pulling on the second suture to position the platform member on the bone tunnel.

Implementations of this aspect may include one or more of the following features.

The pair of sides taper from the trailing edge toward the leading edge. Forming the bone tunnel further includes forming the bone tunnel to interfere with the trailing edge. Forming the bone tunnel to interfere with the trailing edge includes forming the bone tunnel to have an inner diameter that interferes with a dimension of the trailing edge. Pulling on the first suture to pull the tissue graft attachment device through the bone tunnel includes pulling the platform member, leading edge first, through the bone tunnel. Pulling on the second suture to position the platform member on the bone tunnel includes pulling on the second suture to position the platform member at an outlet of the bone tunnel. Pulling on the second suture to position the platform member at an outlet of the bone tunnel includes pulling on the second suture to position the platform member perpendicular to a longitudinal axis of the bone tunnel at the outlet. The method further includes pulling on the first suture to position the platform member on the bone tunnel.

According to yet another aspect, a tissue graft attachment device includes a platform member including a leading edge and a trailing edge connected to the leading edge by a pair of sides that taper from the trailing edge to the leading edge. The platform member defines a pair of slots extending along a central axis passing between the leading edge and the trailing edge, and an opening between the pair of slots and the leading edge. The tissue graft attachment device includes an attachment member passing through the pair of slots to form a loop.

Implementations of this aspect may include one or more of the following features.

The tissue graft attachment device includes a first suture passing through the opening, and a second suture passing through one of the slots.

According to a further aspect, a tissue graft attachment device includes a platform member including a leading edge and a trailing edge connected to the leading edge by a pair of sides. The platform member defines a pair of slots extending along a longitudinal axis passing between the leading edge and the trailing edge, and a surface bounded by the trailing edge, an end of the pair of slots, and the pair of sides, wherein the surface does not include an opening. The tissue graft attachment device includes an attachment member passing through the pair of slots to form a loop.

Implementations of this aspect may include one or more of the following features.

The tissue graft attachment device further includes an opening between the pair of slots and the leading edge.

The details of one or more implementations are set forth in the accompanying drawings and the description below. Other features, aspects, and advantages will become apparent from the description, the drawings, and the claims.

BRIEF DESCRIPTION OF THE DRAWINGS

FIG. 5A is a perspective view of the attachment device being pulled through a bone tunnel.

FIG. 5B is a perspective view of the attachment device of FIG. 5B being positioned on the bone tunnel.

FIG. 5C is a perspective view of an attachment device to which a tissue graft is attached.

Like reference numbers and designations in the various drawings indicate like elements.

DETAILED DESCRIPTION

This document describes an example of an attachment device to attach tissue grafts. The attachment device can be implemented in an endoscopic technique for graft attachment in reconstruction surgery. For example, in an ACL reconstruction surgery, a medial portal incision or a transtibial approach is made and a tunnel is created either from inside the joint space or from the outside. A tissue graft is attached to a platform member included in an attachment device, for example, using looped sutures or a loop of flexible material. The platform member is then passed through the tunnel. After the platform member, in its entirety, exits the tunnel, the attachment device is positioned on the cortex such that the tissue graft passes through the tunnel. A distance between a location at which the looped suture is attached to the platform member and a trailing edge of the platform member may affect the length of loop suture needed to allow the platform member to exit the tunnel in its entirety, which may affect an amount of tissue graft that exits back through the tunnel once the platform member is positioned on the cortex. In various implementations, this distance is minimized or reduced, which may result in an amount of the tissue graft in the tunnel being maximized because shorter loop sutures can be used relative to designs that do not minimize or reduce this distance. Consequently, losses in tissue graft engagement may also be minimized.

Figure 1A:
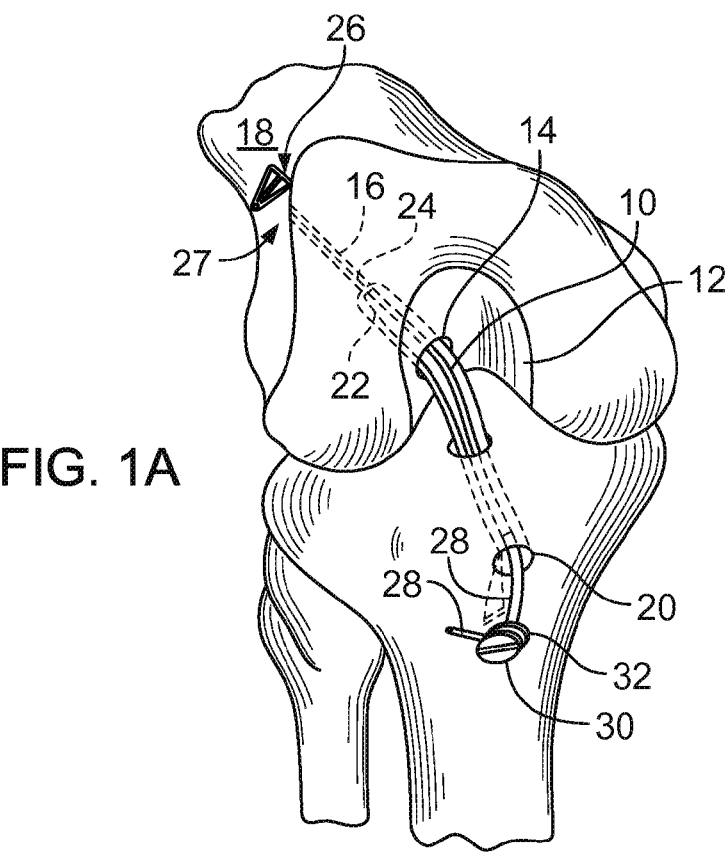
FIGS. 1A and 1B are illustrations of a tissue graft secured within the knee by a graft attachment device.
Figure 1B:
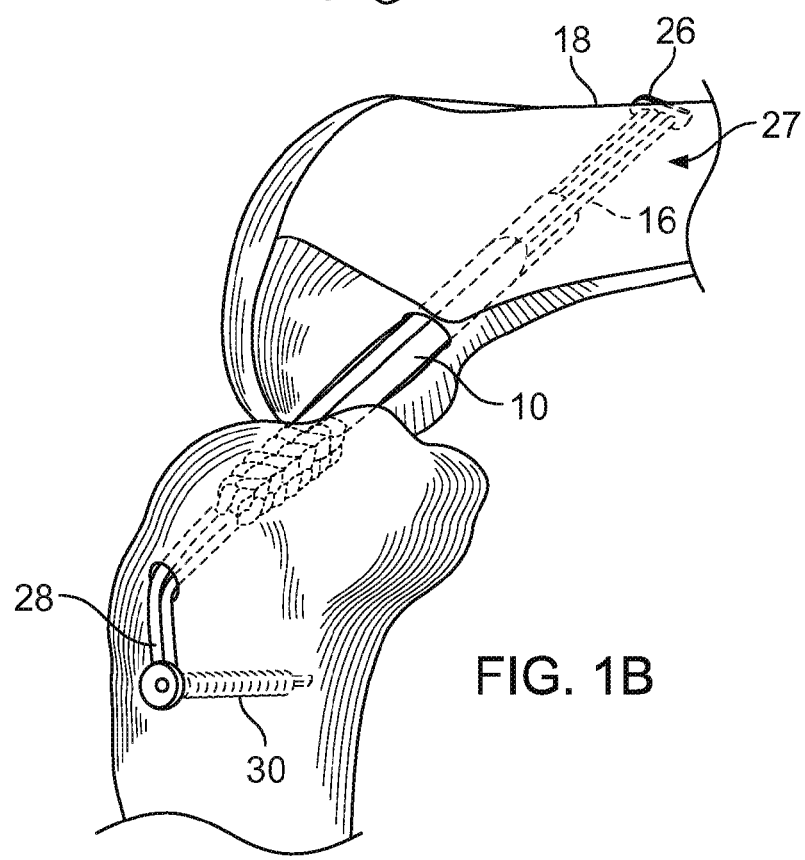

Referring to FIGS. 1A and 1B, a knee joint has a tissue graft 10 (e.g., a patellar tendon graft (FIG. 1A) or a semitendonosis and gracilis graft (FIG. 1B)) implanted in an anterior cruciate ligament (ACL) repair and reconstruction procedure. Prior to implanting tissue graft 10, a notchplasty procedure is preferably performed to expand the intercondylar notch 12 of the femur bone. A femoral channel 14 for receiving one end of tissue graft 10 is then drilled from notch 12 a predetermined distance within the femur with a passing channel 16 of reduced diameter drilled further through the femur from femoral channel 14 to a region of femoral cortex 18. A tibial channel 20 for receiving the other end of tissue graft 10 is drilled from an anterior region of the tibia to a region near the opening of femoral channel 14.

In the case of patellar tendon graft, one end of tissue graft 10 includes a bone block 22 which is shaped and sized in close conformity with femoral channel 14 to ensure optimal healing. A length of suture 24 has one end attached to bone block 22 and the other end secured at femoral cortex region 18 with an attachment device 26. The suture 24 is a woven or braided suture, for example, #5 Ultrabraid suture, attached to the attachment device 26 in a loop configuration. In some implementations described below, one end of the tissue graft 10 is attached to the attachment device 26, which is then pulled through the femoral channel 14. The attachment device 26 may be configured to maximize an amount of the tissue graft 10 in the femoral channel 14. The other end of tissue graft 10 includes a second length of suture 28 which is attached to the tibia, for example, with a fixation screw 30. A washer 32 either attached to or positioned under the head of fixation screw 30 helps in holding the suture in place when screw 30 is tightened.

Figure 2:
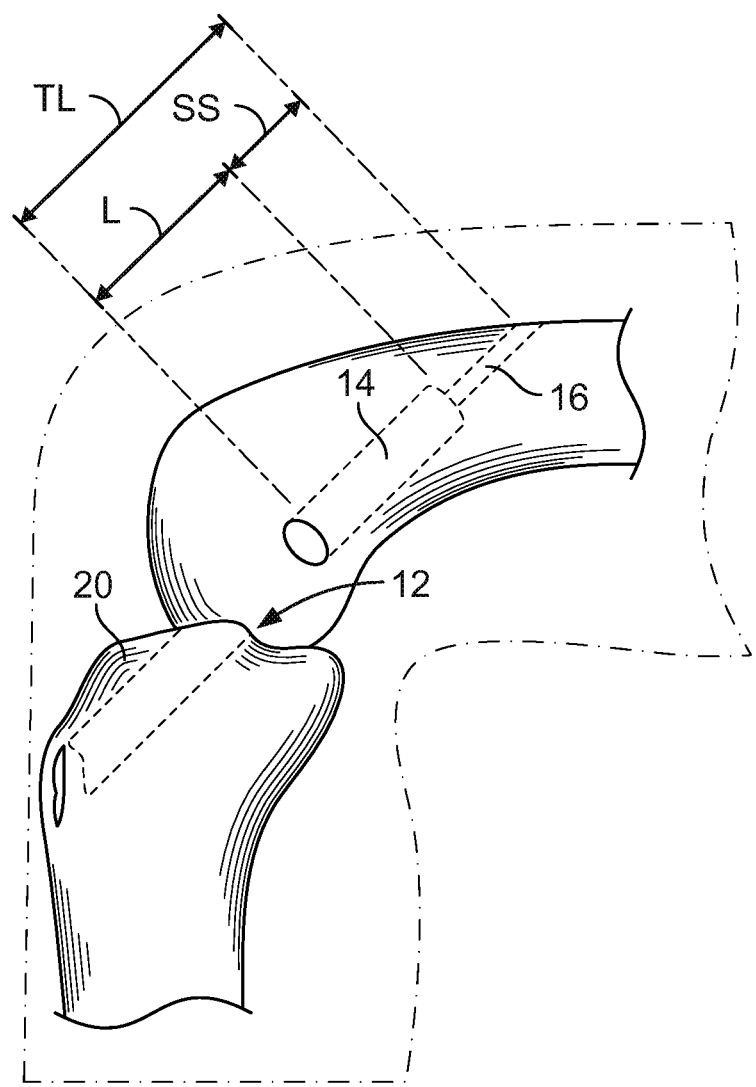
FIG. 2 is another view of the knee joint of FIGS. 1A and 1B.

Referring to FIG. 2, length (L) of femoral channel 14 is selected by the surgeon in accordance with the length of bone block 22 and the desired insertion distance of tissue graft 10 within the femur. The span of suture 24, designated as SS, is approximately that of passing channel 16 so that the sum of the desired insertion length (L) and span of suture (SS) is the measured total length (TL) from the opening of femoral channel 14 to the opening at femoral cortex 18. Each of these dimensions is measured prior to implanting the tissue graft so that during the implantation procedure, the surgeon, under arthroscopic observation, can be assured that tissue graft 10 has been properly positioned within femoral channel 14.

Figure 3:
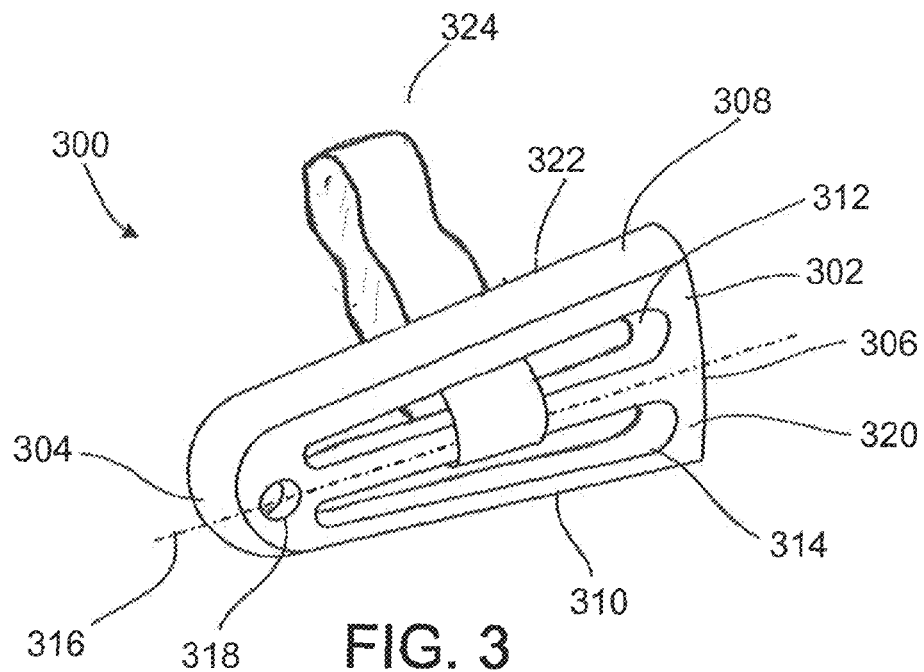
FIG. 3 is a cross-sectional view of a platform member.

FIGS. 3A and 3B are a plan view and a cross-sectional view, respectively, of an example of a platform member 302 that is included in an attachment device (FIG. 4), for example, the attachment device 26. As described below, the attachment device includes a platform member 302 that defines a pair of slots (a first slot 312 and a second slot 314). A tissue graft is attached to the platform member 302 using an attachment member and passed through a bone tunnel, for example, the femoral channel 14. The platform member 302 is configured to maximize the amount of tissue graft passed through the bone tunnel by allowing an attachment member (FIG. 4) to be located close to the trailing edge of the platform member 302 while the platform member 302 is pulled through a bone tunnel. Consequently, a loss of tissue graft engagement in the bone tunnel can be minimized.

The platform member 302 has a length ($L_p$, for example, about 12 mm) and a height ($H_p$, for example, 1.5 mm). The platform member 302 has a leading edge 304 and a trailing edge 306 connected to the leading edge 304 by a pair of sides (a first side 308 and a second side 310). The width ($W_{pl}$) of the platform member 302 near the leading edge 304 is less than the width ($W_{pt}$, for example, about 4 mm) near the trailing edge 306. As described below, the trailing edge 306 is configured to interfere with an inner surface of a bone tunnel, for example, the femoral channel 14, through which the platform member 302 is pulled. The leading edge 304 is curved, for example, substantially semi-circular with a radius of, for example, about 1.75 mm. The trailing edge 306 is less curved relative to the leading edge 304 and is, for example, straight. In alternative implementations, both the leading edge 304 and the trailing edge 306 can be straight.

The first side 308 and the second side 310 are each substantially straight. Further, each side tapers from the trailing edge 306 toward the leading edge 304. A taper of the first side 308 along a longitudinal axis 316 (for example, a central axis) passing between the leading edge 304 and the trailing edge 306 can be the same as or different from a taper of the second side 310 along the longitudinal axis 316. In some implementations, one of the pair of sides (either the first side 308 or the second side 310) can be parallel to the longitudinal axis 316 and the other may not, while in other implementations, the first side 308 and the second side 310 can be parallel to each other and to the longitudinal axis 316.

The platform member 302 defines a pair of slots (a first slot 312 and a second slot 314) extending along the longitudinal axis 316. Each slot 312, 314 is formed on a top surface 320 of the platform member 302 and spans the height of the platform member 302 from the top surface 320 to the bottom surface 322. As described below, each slot 312, 314 is defined by a respective inner trailing edge 332, 340. The inner trailing edges 332, 340 may be formed as near the trailing edge 306 of the platform member 302 as possible, taking into account, for example, machining and manufacturing tolerances, as well as structural integrity. During use, this may minimize or reduce the length of loop suture or other attachment member used to hold the graft.

The first slot 312 is defined by an inner leading edge 330 and an inner trailing edge 332 connected by a pair of inner sides (a first inner side 326 and a second inner side 328). A length of the first slot 312 from the inner leading edge 330 to the inner trailing edge 332 can be, for example, about 7.73 mm. A width of the first slot 312 near the inner leading edge 330 is less than a width near the inner trailing edge 332. In some implementations, the width of the first slot 312 is sufficient to pass the attachment member (FIG. 4) or a suture (FIG. 4) or both through the first slot 312. Each of the inner leading edge 330 and the inner trailing edge 332 is curved and, for example, has a semi-circular cross-section. For example, a radius of curvature of the inner leading edge 330 and the inner trailing edge is about 0.38 mm and 0.51 mm, respectively. Alternatively, one or both of the first inner leading edge 330 and the inner trailing edge 332 can be straight.

The first inner side 326 and the second inner side 328 are formed between the longitudinal axis 316 and the first side 308 such that the first inner side 326 is closer to the first side 308 than to the longitudinal axis 316, and the second inner side 328 is closer to the longitudinal axis 316 than to the first side 308. In some implementations, the first inner side 326 is parallel to the longitudinal axis 316 and the second inner side 328 is parallel to the first side 308. Because the first side 308 tapers from the trailing edge 306 toward the leading edge 304 along a longitudinal axis 334 of the first slot 312, in such implementations, the first inner side 326 and the second inner side 328 may not be parallel to each other. Alternatively, each of the pair of inner sides 326, 328 can be parallel to each other and to either the first side 308 or the longitudinal axis 316.

The second slot 314 is formed on the platform member 302 in a manner similar to the first slot 312 but on the opposite side of the longitudinal axis 316. In some implementations, the second slot 314 is a mirror image of the first slot 312 about the longitudinal axis 316, and is defined by an inner leading edge 338 and an inner trailing edge 340 connected by a pair of inner sides (a first inner side 342 and a second inner side 344) along the longitudinal axis 316. The trailing edge 306, an end of the pair of slots 312, 314, and the pair of sides 308, 310 define a surface 350 that does not include an opening. For example, the surface 350 is bounded by the trailing edge 306, the inner trailing edges 332, 340 of the pair of slots 312, 314, and the pair of sides 308, 310.

The platform member 302 additionally defines an opening 318 between the pair of slots 312, 314 and the leading edge 304. The opening 318 is formed on the top surface 320 of the platform member 302 and spans a height of the platform member 302 from the top surface 320 to the bottom surface 322. In some implementations, the opening 318 is formed on the longitudinal axis 316. The opening 318 has a substantially circular cross-section. In alternative implementations, the cross-section of the opening 318 can be, for example, rectangular, elliptical, and the like. A cross-sectional dimension of the opening 318 is sufficient to receive a suture to pull the platform member 302 through the bone tunnel. For example, a diameter of the opening 318 can be about 1 mm.

Figure 4:
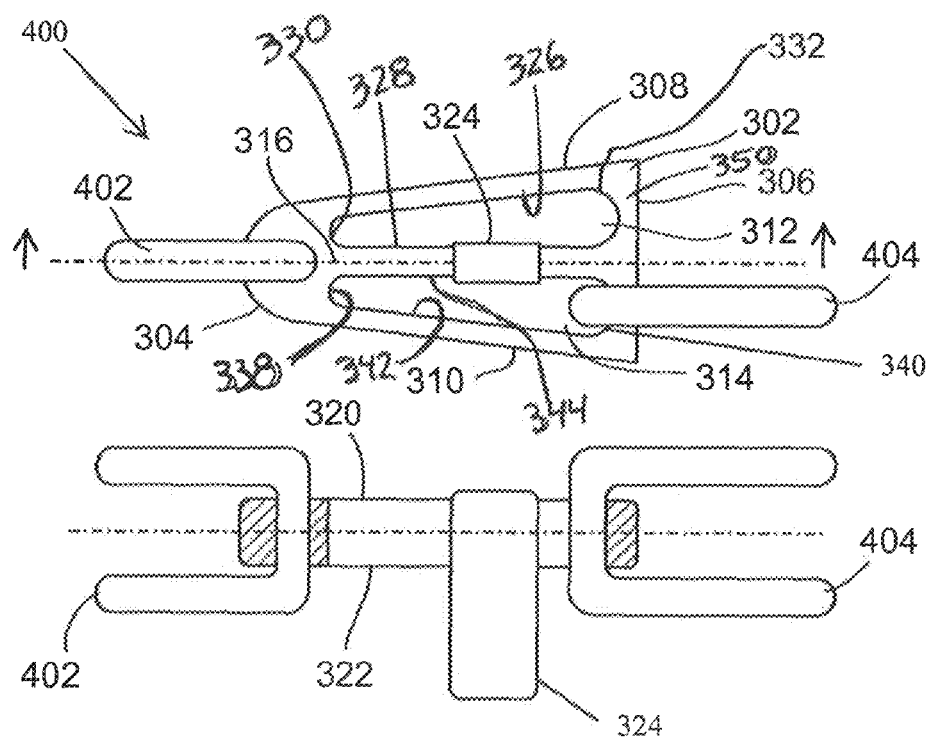
FIG. 4 is a perspective view of an attachment device that includes the platform member of FIG. 3.

FIG. 4 is a perspective view of an attachment device 400, which includes the platform member 302 and an attachment member 324 passing through the pair of slots (the first slot 312 and the second slot 314) to form a loop. The attachment member 324 can be made from a flexible material that can be formed into a loop. For example, the attachment member 324 can be approximately 10 mm long in an un-stretched state and approximately 50 mm long in a stretched state. In some implementations, the attachment member 324 is a suture, while, in others, the attachment member 324 is an elastic band. An end of the tissue graft is attached to the loop (324). A length of the attachment member 324 may be chosen such that the end of the tissue graft is located as close to the platform member 302 as possible, while still allowing the platform member 302 to exit the bone tunnel. This may maximize a length of engagement of the tissue graft.

In some implementations, the attachment device 400 can be pre-loaded to include a first suture 402 and a second suture 404. Specifically, the first suture 402 is passed through the opening 318 and the second suture 404 is passed through either the first slot 312 or the second slot 314 or, in some situations, looped through both slots 312 and 314. In some implementations, the platform member 302 may not define an opening between the pair of slots 312, 314 and the leading edge 304. In such implementations, the first suture 402 and the second suture 404 can be passed through either the first slot 312 or the second slot 314, or both.

FIGS. 5A and 5B are perspective views of the attachment device 400 to which a tissue graft 520 is attached, being pulled through and positioned on a bone tunnel 500, for example, the femoral channel 14. The bone tunnel 500 can be, for example, 3.5 mm in diameter and have a substantially vertical or angular orientation. A tissue graft 520 is attached to the attachment member 324. The attachment device 400 is then passed through the bone tunnel 500. To do so, the first suture 402, which was passed through the opening 318, is pulled through the bone tunnel 500, causing the leading edge 304 of the platform member 302 to first pass through the bone tunnel 500 followed by the trailing edge 306. The attachment member 324 that is passed through the pair of slots 312, 314 trails the leading edge 306. Because the tissue graft 520 is attached to the loop (324), pulling on the first suture 402 causes the tissue graft 520 to be passed through the bone tunnel 500. Similarly, because the second suture 404 is attached to the either or both slots 312, 314, pulling on the first suture 402 also causes the second suture 404 to be passed through the bone tunnel 500.

As the platform member 302 is pulled through the bone tunnel 500, the loop (324) slides towards and rests against the inner trailing edges 332, 340 of the first slot 312 and the second slot 314, respectively. As described above, the inner trailing edge 332 of the first slot 312 and the inner trailing edge 340 of the second slot 314 may each be formed as near the trailing edge 306 as possible. Because the loop (324) moves to the inner trailing edge 340, the length of loop (324) needed is shorter than if the loop (324) was connected elsewhere on the platform member (for example, the center). This is the result of the loop (324) needing to be longer at other attachment points to allow the platform member 302 to fully exit the tunnel 500. A shorter loop (324) can result in a greater engagement of the tissue graft with the bone when compared to a longer loop (324).

When the platform member 302 exits the outlet 502 of the bone tunnel 500, the inner trailing edges 332, 340 first exit the outlet 502 followed by the trailing edge 306. The second suture 404 can be pulled out of the outlet 502. After the platform member 302 exits the outlet in its entirety, the platform member 302 is positioned on a bone surface 504 of the bone tunnel 500, for example, the cortex of the femoral channel 14. To do so, the platform member 302 is flipped until a portion of either the top surface 320 or the bottom surface 322 rests on the bone surface 504. As shown in FIG. 5B, the second suture 404 is pulled, for example, in a direction transverse to a longitudinal axis of the bone tunnel 500, to position the platform member 302 on the bone surface 504. For example, after the platform member 302 has been flipped and rested on the bone surface 504, either the first suture 402 or the second suture 404 or both can be pulled to slide the platform member 302 on the bone surface 504 until the platform member 302 is substantially centered in the bone tunnel 500. Once positioned, the longitudinal axis 316 of the platform member 302 can be perpendicular to a longitudinal axis of the bone tunnel 500. FIG. 5C is a perspective view of an attachment device 400 to which a tissue graft 520 is attached. By sliding the platform member 302 using either the first suture 402 or the second suture 404 or both along the bone surface 504, the position of the tissue graft 520 in the bone tunnel 500 can be centered.

While this specification contains many specific implementation details, these should not be construed as limitations on the scope of any implementations or of what may be claimed, but rather as descriptions of features specific to particular implementations of particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Thus, particular implementations of the subject matter have been described. Other implementations are within the scope of the following claims.

The invention claimed is:

1. A tissue graft attachment device comprising:
    a platform member having a central axis and including a leading edge and a trailing edge connected to the leading edge by a pair of sides, the platform member defining:
        i) a pair of elongated slots extending along the central axis between the leading edge and the trailing edge, the elongated slots being located on opposite sides of the central axis and positioned to form a central member in-line with the central axis, each elongated slot comprising a respective inner leading edge; and
        ii) one and only one circular opening defined in the platform member, the one and only one circular opening positioned in-line with the central axis between the inner leading edges of the elongated slots in the pair of elongated slots and the platform leading edge;
    a first suture passing through the circular opening;
    a second suture passing through one of the elongated slots; and
    an attachment member passing through each elongated slot in the pair of elongated slots and forming a loop around the central member.

2. The device of claim 1, wherein the leading edge is substantially curved; and wherein a length of the elongated slots along the central axis is greater than a width of the attachment member, the attachment member free to move in the elongated slots along the central member.

3. The device of claim 1, wherein the leading edge is substantially semi-circular.

4. The device of claim 1, wherein the attachment member is an elastic band.

5. The device of claim 1, wherein an outer surface of the sides of the platform member are smooth to facilitate passage of the platform member through a bone tunnel.

6. The device of claim 5, wherein the first suture and the second suture facilitate orientation of the central axis in a direction transverse to a longitudinal axis of a bone tunnel through which the platform member is pulled, a tissue graft coupled to the attachment member, the attachment member extending through the bone tunnel.

7. The device of claim 6, wherein the platform member rests on a surface of the bone over the bone tunnel, the platform member anchored with respect to the surface the bone tunnel.

8. A method of attaching a tissue graft, the method comprising:
    providing a tissue graft attachment device that includes:
        a platform member having a central axis and including a leading edge and a trailing edge connected to the leading edge by a pair of sides, the platform member defining:
            a pair of elongated slots extending along the central axis between the leading edge and the trailing edge, the elongated slots being located on opposite sides of the central axis and positioned to form a central member in-line with the central axis, each elongated slot comprising a respective inner leading edge; and
            one and only one circular opening defined in the platform member, the one and only one circular opening positioned in-line with the central axis between the inner leading edges of the elongated slots in the pair of elongated slots and the platform leading edge,
        a first suture passing through the circular opening,
        a second suture passing through one of the elongated slots, and
        an attachment member passing through each of the elongated slots in the pair and forming a loop around the central member;
    forming a bone tunnel;
    pulling on the first suture to pull the platform member through the bone tunnel; and
    pulling on the second suture to position the platform member on the bone tunnel.

9. The device of claim 1, wherein the pair of elongated slots includes a first elongated slot and a second elongated slot, the second suture passing through the first elongated slot, the attachment member passing through both the first elongated slot and the second elongated slot to form the loop;
    wherein the first elongated slot includes a first end and a second end, the first end located towards the leading edge, the second end located towards the trailing edge; and
    wherein the second suture resides at the second end of the first elongated slot.

10. The device as in claim 9, wherein the loop formed by the attachment member resides in a middle of the first elongated slot between the first end and the second end.

11. The tissue graft attachment device as in claim 1, wherein the platform is arrowhead-shaped.

12. The tissue graft attachment device as in claim 11, wherein the pair of elongated slots includes a first elongated slot and a second elongated slot, the first elongated slot narrowing from trailing edge to the leading edge, the second elongated slot narrowing from the trailing edge to the leading edge.

13. The tissue graft attachment device of claim 1, wherein each elongated slot further comprises:
a respective inner leading edge, first and second inner sides and an inner trailing edge,
wherein the first inner sides are parallel to the central axis and the second inner sides are not parallel to the central axis.

14. The tissue graft attachment device of claim 1, wherein:
each elongated slot further comprises a respective inner trailing edge,
wherein each respective inner trailing edge is formed as near the platform member trailing edge as is possible.

15. The method device of claim 8, wherein the pair of elongated slots includes a first elongated slot and a second elongated slot, the second suture passing through the first elongated slot, a length of the attachment member passing through both the first elongated slot and the second elongated slot;
wherein the first elongated slot includes a first end and a second end, the first end located towards the leading edge, the second end located towards near the trailing edge; and
wherein the second suture resides at the second end of the first elongated slot.

16. The method of claim 8, wherein the pair of sides taper from the trailing edge toward the leading edge, and wherein forming the bone tunnel further comprises forming the bone tunnel to interfere with the trailing edge.

17. The method of claim 16, wherein forming the bone tunnel to interfere with the trailing edge comprises forming the bone tunnel to have an inner diameter that interferes with a dimension of the trailing edge.

18. The method of claim 16, wherein pulling on the first suture to pull the tissue graft attachment device through the bone tunnel comprises pulling the platform member, leading edge first, through the bone tunnel.

19. The method of claim 8, wherein pulling on the second suture to position the platform member on the bone tunnel comprises pulling on the second suture to position the platform member at an outlet of the bone tunnel.

20. The method of claim 19, wherein pulling on the second suture to position the platform member at an outlet of the bone tunnel comprises pulling on the second suture to position the platform member perpendicular to a longitudinal axis of the bone tunnel at the outlet.

* * * * *